(12) United States Patent
Quick et al.

(10) Patent No.: US 8,460,204 B2
(45) Date of Patent: Jun. 11, 2013

(54) BIOPSY DEVICE WITH INNER CUTTING MEMBER

(75) Inventors: Richard L. Quick, Mission Viejo, CA (US); Frank R. Louw, Carlsbad, CA (US); Paul Lubock, Laguna Niguel, CA (US); Martin V. Shabaz, Lake Forest, CA (US)

(73) Assignee: Senorx, Inc., Tempe, AZ (US)

( * ) Notice: Subject to any disclaimer, the term of this patent is extended or adjusted under 35 U.S.C. 154(b) by 0 days.

(21) Appl. No.: 12/793,465

(22) Filed: Jun. 3, 2010

(65) Prior Publication Data

US 2010/0262037 A1  Oct. 14, 2010

Related U.S. Application Data

(63) Continuation of application No. 10/642,406, filed on Aug. 15, 2003, now Pat. No. 7,819,819, which is a continuation-in-part of application No. 10/374,915, filed on Feb. 24, 2003, now Pat. No. 7,189,206.

(51) Int. Cl.
*A61B 10/00* (2006.01)

(52) U.S. Cl.
USPC .......................................... 600/564

(58) Field of Classification Search
USPC .................. 600/564, 565, 566; 606/180, 167, 606/159
See application file for complete search history.

(56) References Cited

U.S. PATENT DOCUMENTS

| | | |
|---|---|---|
| 2,032,860 A | 3/1936 | Wappler et al. |
| 3,326,785 A | 6/1967 | Williams |
| 3,805,791 A | 4/1974 | Seuberth et al. |
| 3,844,272 A | 10/1974 | Banko |
| 3,847,153 A | 11/1974 | Weissman |
| 3,902,498 A | 9/1975 | Niederer |
| 3,910,279 A | 10/1975 | Okada et al. |
| 3,945,375 A | 3/1976 | Banko |
| 3,955,578 A | 5/1976 | Chamness et al. |
| 4,007,732 A | 2/1977 | Kvavle et al. |
| 4,202,338 A | 5/1980 | Bitrolf |
| 4,243,048 A | 1/1981 | Griffin |
| 4,294,254 A | 10/1981 | Chamness |

(Continued)

FOREIGN PATENT DOCUMENTS

| | | |
|---|---|---|
| CH | 602084 A5 | 6/1976 |
| DE | 195 28 440 | 8/1995 |

(Continued)

*Primary Examiner* — Brian Szmal
*Assistant Examiner* — Fangemonique Smith

(57) ABSTRACT

The invention is directed to devices and methods for separating and collecting a tissue specimen from a patient's target site. The device includes a probe member with a penetrating distal tip and a tissue receiving aperture, and a tissue cutting member which is rotatable disposed within the probe member to cut a tissue specimen drawn into the interior of the device through the aperture. The longitudinal edges of the aperture are preferably sharpened to engage the cutting edges of the tissue cutting member. Vacuum may be provided in the inner lumen of the cutting member to transport tissue therethrough. Rotation, rotational oscillation and/or longitudinal reciprocation of the tissue cutting member is effective to separate a tissue specimen from surrounding tissue. An accessing cannula having an tissue receiving aperture may be concentrically disposed within the probe member and about the tissue cutting member. The tissue cutting edge of the tissue cutting member preferably is longitudinally oriented and may have a cutting angle less than 90° with respect to the longitudinal axis of the tissue cutting member.

3 Claims, 11 Drawing Sheets

U.S. PATENT DOCUMENTS

| | | | |
|---|---|---|---|
| 4,311,143 A | | 1/1982 | Komiya |
| 4,362,160 A | | 12/1982 | Hiltebrandt |
| 4,503,855 A | | 3/1985 | Maslanka |
| 4,565,200 A | | 1/1986 | Cosman |
| 4,576,162 A | | 3/1986 | McCorkle |
| 4,603,694 A | | 8/1986 | Wheeler |
| 4,638,802 A | | 1/1987 | Okada |
| 4,643,187 A | | 2/1987 | Okada |
| 4,660,267 A | * | 4/1987 | Wheeler ................ 29/437 |
| 4,682,606 A | | 7/1987 | DeCaprio |
| 4,718,419 A | | 1/1988 | Okada |
| 4,724,836 A | | 2/1988 | Okada |
| 4,800,896 A | | 1/1989 | Jalowayski |
| 4,926,858 A | | 5/1990 | Gifford, III et al. |
| 5,007,908 A | | 4/1991 | Rydell |
| 5,041,124 A | | 8/1991 | Kensey |
| 5,047,027 A | | 9/1991 | Rydell |
| 5,059,204 A | | 10/1991 | Lawson et al. |
| 5,064,424 A | | 11/1991 | Bitrolf |
| 5,080,660 A | | 1/1992 | Buelna |
| 5,085,659 A | | 2/1992 | Rydell |
| RE33,925 E | | 5/1992 | Bales et al. |
| 5,133,359 A | | 7/1992 | Kedem |
| 5,133,360 A | | 7/1992 | Spears |
| RE34,056 E | | 9/1992 | Lindgren et al. |
| 5,158,561 A | | 10/1992 | Rydell et al. |
| 5,217,458 A | | 6/1993 | Parins |
| 5,219,350 A | | 6/1993 | Emerson et al. |
| 5,320,613 A | | 6/1994 | Houge et al. |
| 5,324,288 A | | 6/1994 | Billings et al. |
| 5,335,671 A | | 8/1994 | Clement |
| 5,344,420 A | | 9/1994 | Hilal et al. |
| 5,366,468 A | | 11/1994 | Fucci et al. |
| 5,374,188 A | | 12/1994 | Frank et al. |
| 5,380,321 A | | 1/1995 | Yoon |
| 5,395,312 A | | 3/1995 | Desai |
| 5,415,656 A | | 5/1995 | Tihon et al. |
| 5,417,687 A | | 5/1995 | Nardella et al. |
| 5,423,809 A | | 6/1995 | Klicek |
| 5,437,665 A | | 8/1995 | Munro |
| 5,441,498 A | | 8/1995 | Perkins |
| 5,441,503 A | | 8/1995 | Considine et al. |
| 5,470,308 A | | 11/1995 | Edwards et al. |
| 5,476,102 A | | 12/1995 | Como et al. |
| 5,477,862 A | | 12/1995 | Haaga |
| 5,488,958 A | | 2/1996 | Topel et al. |
| 5,501,654 A | | 3/1996 | Failla et al. |
| 5,507,743 A | | 4/1996 | Edwards et al. |
| 5,526,822 A | | 6/1996 | Burbank et al. |
| 5,527,331 A | | 6/1996 | Kresch et al. |
| 5,538,010 A | | 7/1996 | Darr et al. |
| 5,575,794 A | | 11/1996 | Walus et al. |
| 5,578,030 A | | 11/1996 | Levin |
| 5,595,185 A | | 1/1997 | Erlich et al. |
| 5,599,347 A | | 2/1997 | Hilal et al. |
| 5,607,389 A | | 3/1997 | Edwards et al. |
| 5,649,547 A | | 7/1997 | Ritchart et al. |
| 5,653,718 A | | 8/1997 | Yoon |
| 5,674,184 A | | 10/1997 | Hassler, Jr. |
| 5,676,663 A | | 10/1997 | Kim |
| 5,683,384 A | | 11/1997 | Gough et al. |
| 5,687,739 A | | 11/1997 | McPherson et al. |
| 5,769,086 A | | 6/1998 | Ritchart et al. |
| 5,772,660 A | | 6/1998 | Young et al. |
| 5,775,333 A | | 7/1998 | Burbank et al. |
| 5,782,775 A | | 7/1998 | Milliman et al. |
| 5,794,626 A | | 8/1998 | Kieturakis |
| 5,797,907 A | | 8/1998 | Clement |
| 5,810,806 A | | 9/1998 | Ritchart et al. |
| 5,814,044 A | | 9/1998 | Hooven |
| 5,846,513 A | | 12/1998 | Carroll et al. |
| 5,848,978 A | | 12/1998 | Cecchi |
| 5,857,981 A | | 1/1999 | Bucalo et al. |
| 5,857,982 A | | 1/1999 | Milliman et al. |
| 5,871,454 A | | 2/1999 | Majlessi |
| 5,873,886 A | | 2/1999 | Larsen et al. |
| 5,876,340 A | | 3/1999 | Tu et al. |
| 5,882,316 A | | 3/1999 | Chu et al. |
| 5,902,272 A | | 5/1999 | Eggers et al. |
| 5,913,857 A | | 6/1999 | Ritchart et al. |
| 5,925,044 A | | 7/1999 | Hofmann et al. |
| 5,928,164 A | | 7/1999 | Burbank et al. |
| 5,947,964 A | | 9/1999 | Eggers et al. |
| 5,954,670 A | | 9/1999 | Baker |
| 5,964,716 A | | 10/1999 | Gregoire et al. |
| 5,980,469 A | | 11/1999 | Burbank et al. |
| 5,984,919 A | | 11/1999 | Hilal et al. |
| 5,997,560 A | | 12/1999 | Miller |
| 6,036,681 A | | 3/2000 | Hooven |
| 6,050,955 A | | 4/2000 | Bryan et al. |
| 6,056,700 A | | 5/2000 | Burney et al. |
| 6,077,230 A | | 6/2000 | Gregoire et al. |
| 6,086,543 A | | 7/2000 | Anderson et al. |
| 6,120,462 A | | 9/2000 | Hibner et al. |
| 6,142,955 A | | 11/2000 | Farascioni et al. |
| 6,176,865 B1 | | 1/2001 | Mauze et al. |
| 6,220,248 B1 | | 4/2001 | Voegele et al. |
| 6,258,000 B1 | | 7/2001 | Liechty, II |
| 6,258,111 B1 | | 7/2001 | Ross et al. |
| 6,261,241 B1 | | 7/2001 | Burbank et al. |
| 6,261,302 B1 | | 7/2001 | Voegele et al. |
| 6,277,083 B1 | | 8/2001 | Eggers et al. |
| 6,312,429 B1 | | 11/2001 | Burbank et al. |
| 6,331,166 B1 | | 12/2001 | Burbank et al. |
| 6,344,026 B1 | | 2/2002 | Burbank et al. |
| 6,350,244 B1 | | 2/2002 | Fisher |
| 6,454,727 B1 | | 9/2002 | Burbank et al. |
| 6,494,881 B1 | | 12/2002 | Bales et al. |
| 6,514,215 B1 | | 2/2003 | Ouchi |
| 6,514,248 B1 | | 2/2003 | Eggers et al. |
| 6,540,695 B1 | | 4/2003 | Burbank et al. |
| 6,562,032 B1 | | 5/2003 | Ellman et al. |
| 6,575,991 B1 | | 6/2003 | Chesbrough et al. |
| 6,589,157 B2 | | 7/2003 | Fontayne et al. |
| 6,689,145 B2 | | 2/2004 | Lee et al. |
| 6,712,773 B1 | | 3/2004 | Viola |
| 6,712,775 B2 | | 3/2004 | Burbank et al. |
| 6,758,824 B1 | | 7/2004 | Miller et al. |
| 6,835,173 B2 | | 12/2004 | Couvillon, Jr. |
| 6,994,667 B2 | | 2/2006 | Singh |
| 7,189,206 B2 | | 3/2007 | Quick et al. |
| 7,226,424 B2 | | 6/2007 | Ritchart et al. |
| 7,452,357 B2 | | 11/2008 | Vlegele et al. |
| 2001/0002250 A1 | | 5/2001 | Burbank et al. |
| 2002/0022768 A1 | | 2/2002 | Utsui |
| 2002/0143270 A1 | | 10/2002 | Miller |
| 2003/0004407 A1 | | 1/2003 | Carroll et al. |
| 2003/0125639 A1 | | 7/2003 | Fisher et al. |
| 2003/0199760 A1 | | 10/2003 | Curpen et al. |
| 2003/0236471 A1 | | 12/2003 | Fisher |
| 2004/0019299 A1 | | 1/2004 | Ritchart et al. |
| 2004/0024304 A1 | | 2/2004 | Foerster et al. |

FOREIGN PATENT DOCUMENTS

| | | |
|---|---|---|
| DE | 10066004 A1 | 12/2000 |
| EP | 0 146 699 | 9/1984 |
| EP | 0 255 123 | 2/1988 |
| EP | 0 472 368 | 8/1991 |
| EP | 0 509 670 | 10/1992 |
| EP | 0 601 709 | 6/1994 |
| EP | 0 769 281 | 4/1997 |
| EP | 0 858 774 | 8/1998 |
| EP | 0 919 190 | 6/1999 |
| EP | 0 966 925 | 12/1999 |
| EP | 0 970 658 | 1/2000 |
| EP | 1072288 A2 | 1/2001 |
| GB | 1 225 813 | 9/1966 |
| GB | 1571926 | 7/1980 |
| GB | 2 311 468 | 10/1997 |
| WO | 9207500 A2 | 5/1992 |
| WO | WO 93/13718 | 7/1993 |
| WO | WO 95/02370 | 1/1995 |
| WO | WO 95/02371 | 1/1995 |
| WO | WO95/03843 | 2/1995 |
| WO | WO 97/29702 | 8/1997 |
| WO | 9742887 | 11/1997 |
| WO | WO 98/08441 | 3/1998 |

| WO | 9846147 A1 | 10/1998 |
| WO | WO 98/43531 | 10/1998 |
| WO | WO 99/44506 | 9/1999 |
| WO | WO 00/12009 | 3/2000 |
| WO | WO 00 16697 | 3/2000 |
| WO | 0128631 A1 | 4/2001 |
| WO | WO 01/49184 | 7/2001 |
| WO | 0158505 A2 | 8/2001 |
| WO | WO 02/22023 | 3/2002 |
| WO | WO 02062227 A1 * | 8/2002 |
| WO | 02074214 A1 | 9/2002 |
| WO | WO 2004/052212 | 6/2004 |
| WO | 2005020925 A2 | 3/2005 |
| WO | WO 2005/063126 | 7/2005 |
| WO | WO 2006/049911 | 5/2006 |

* cited by examiner

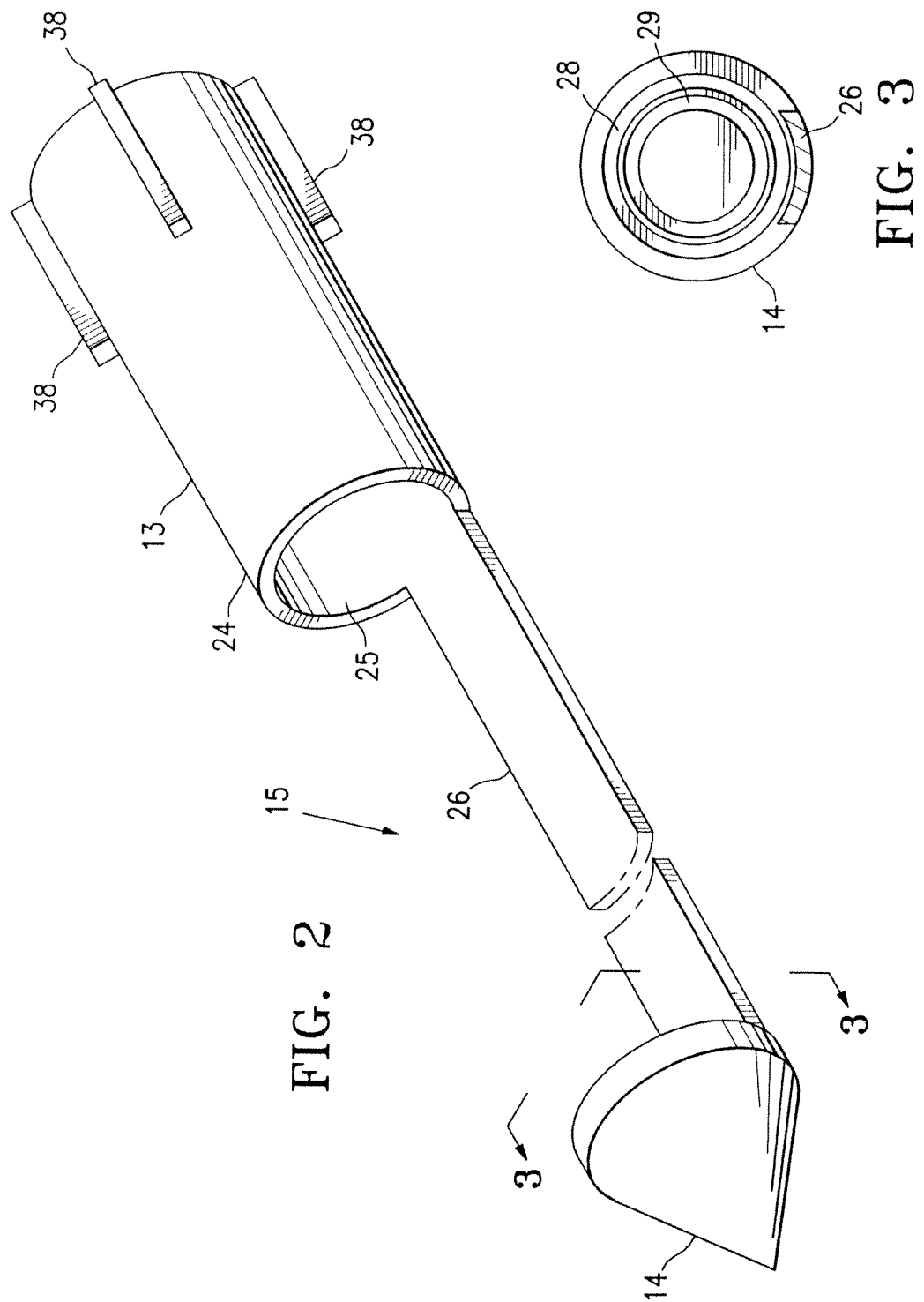

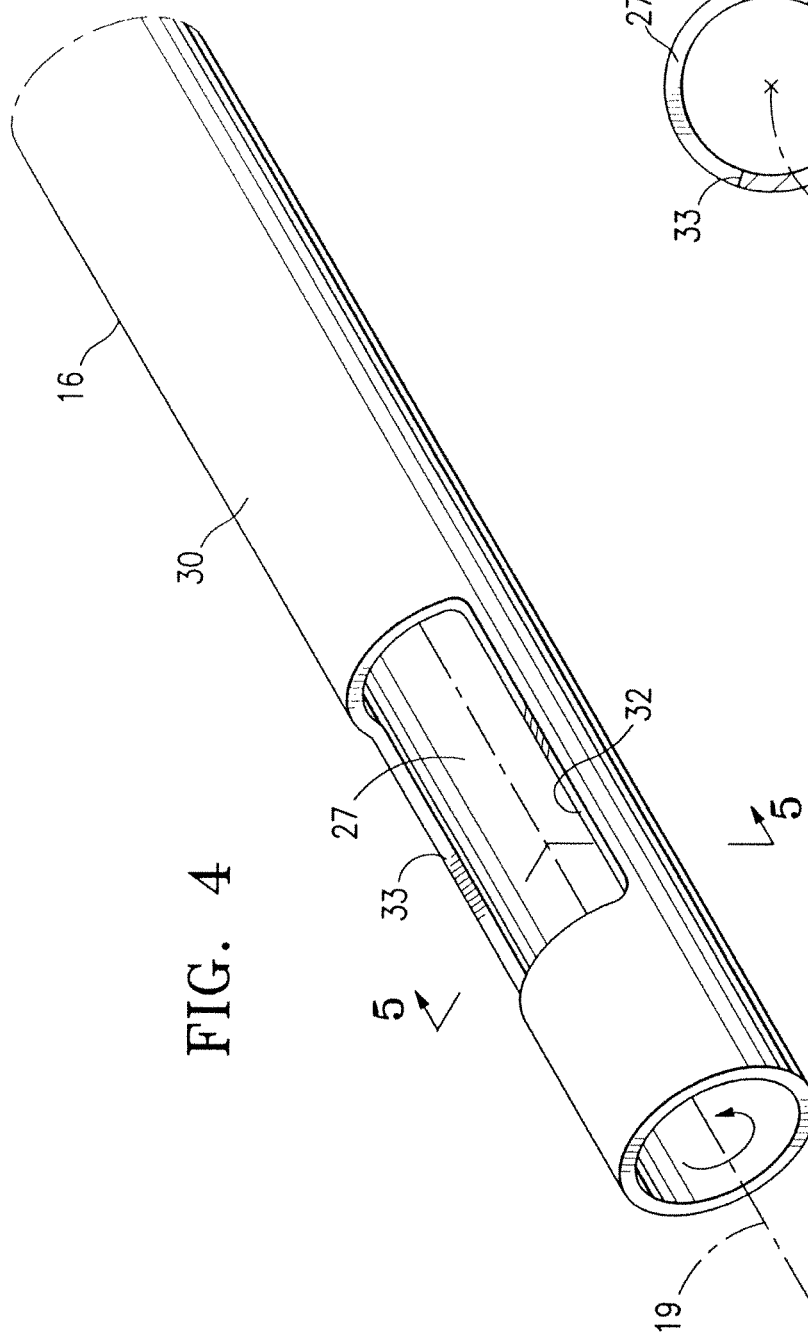
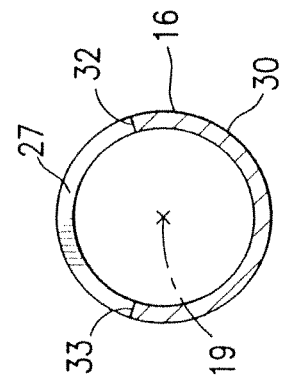
FIG. 4
FIG. 5

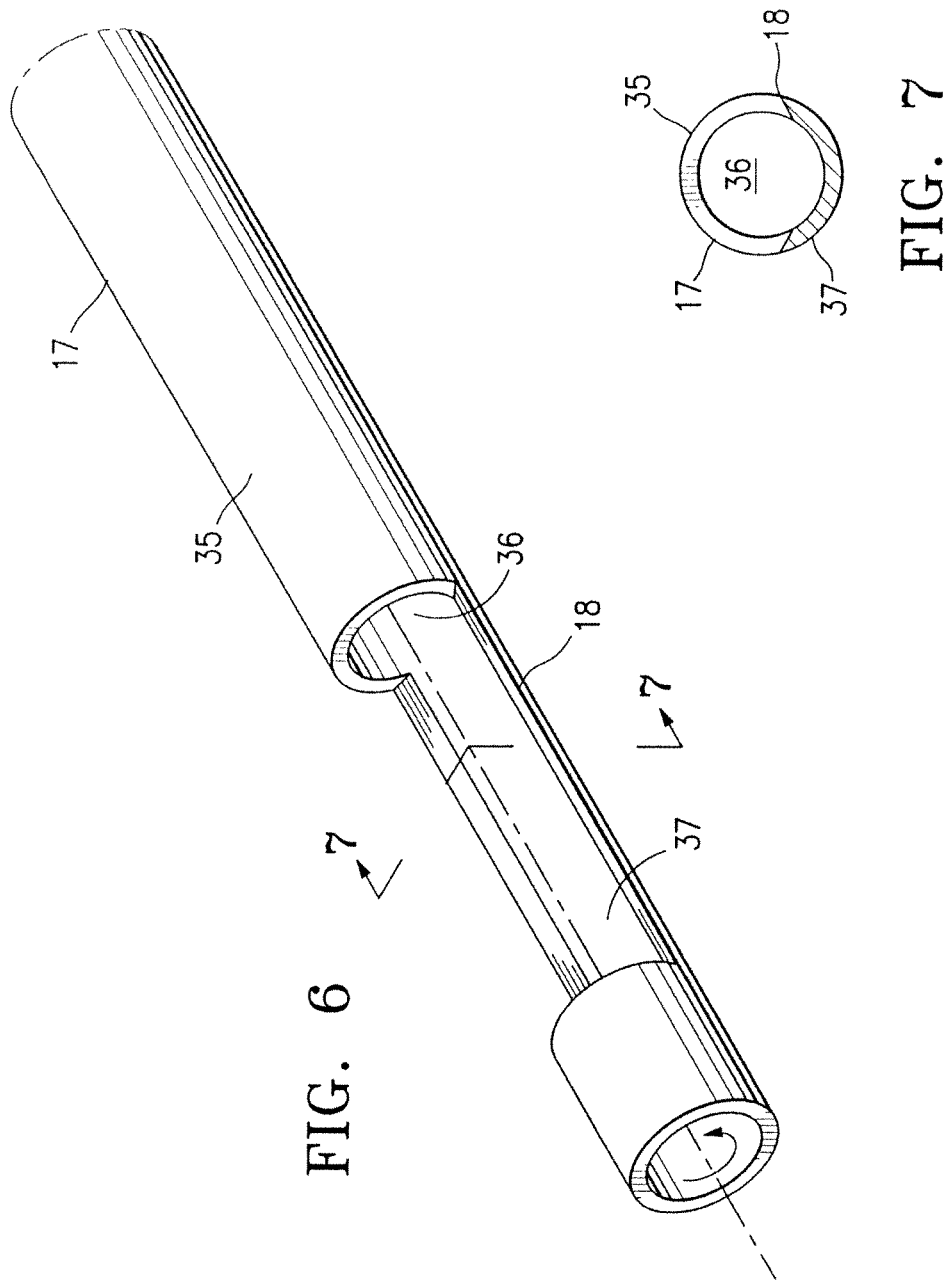

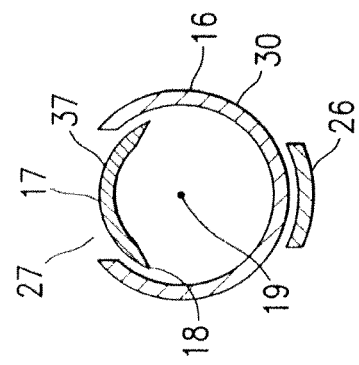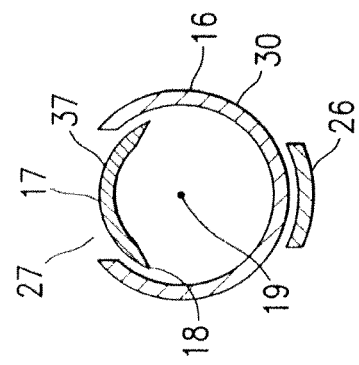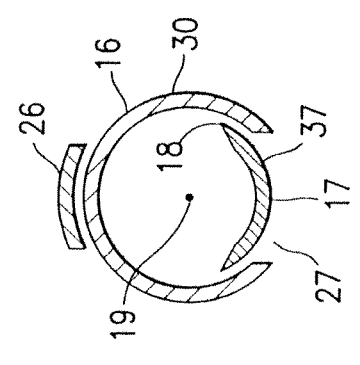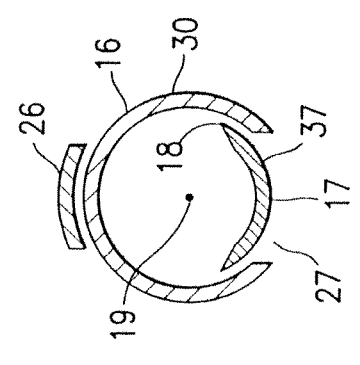
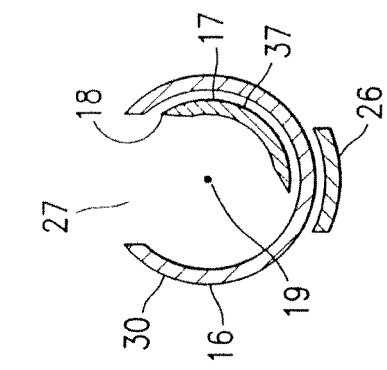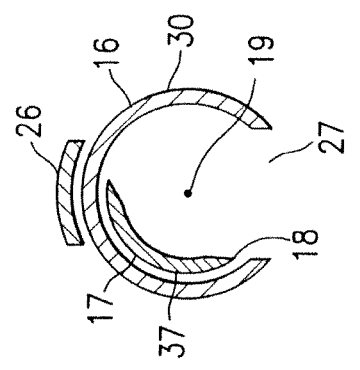
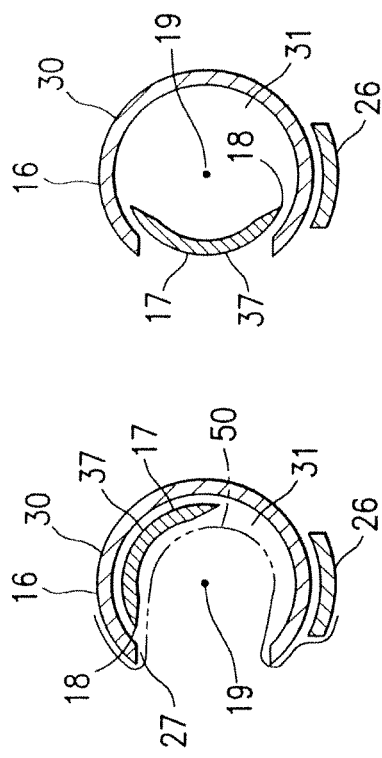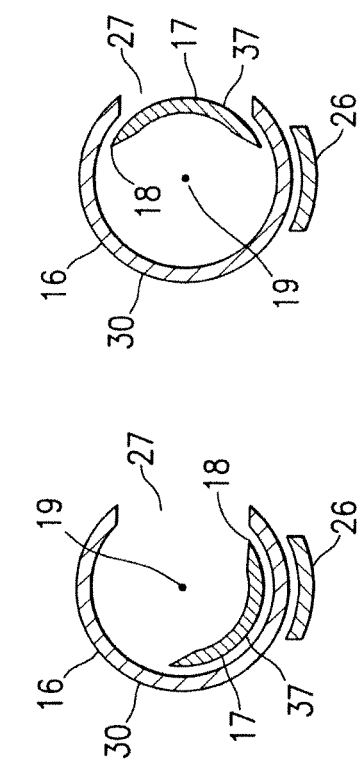

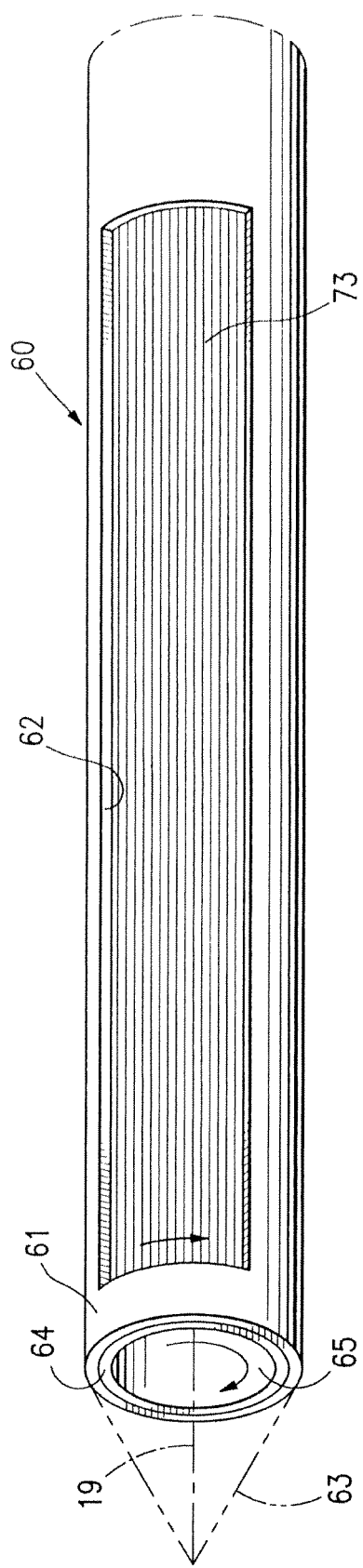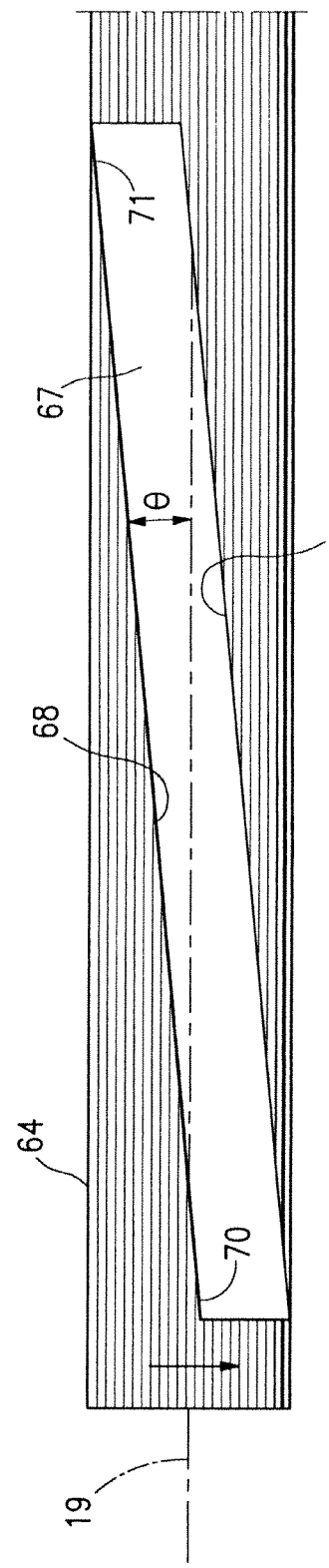
FIG. 13
FIG. 14

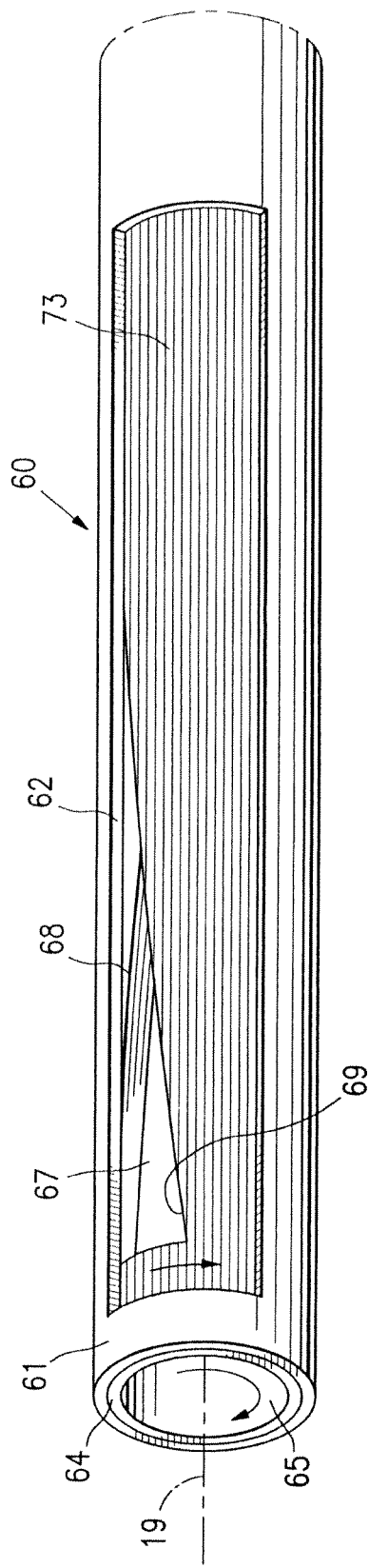
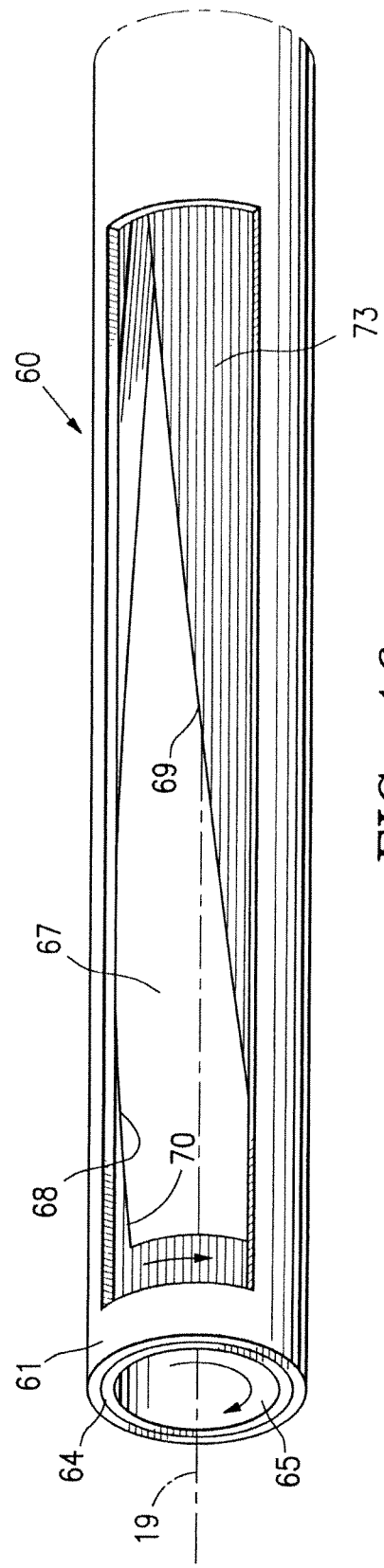
FIG. 15
FIG. 16

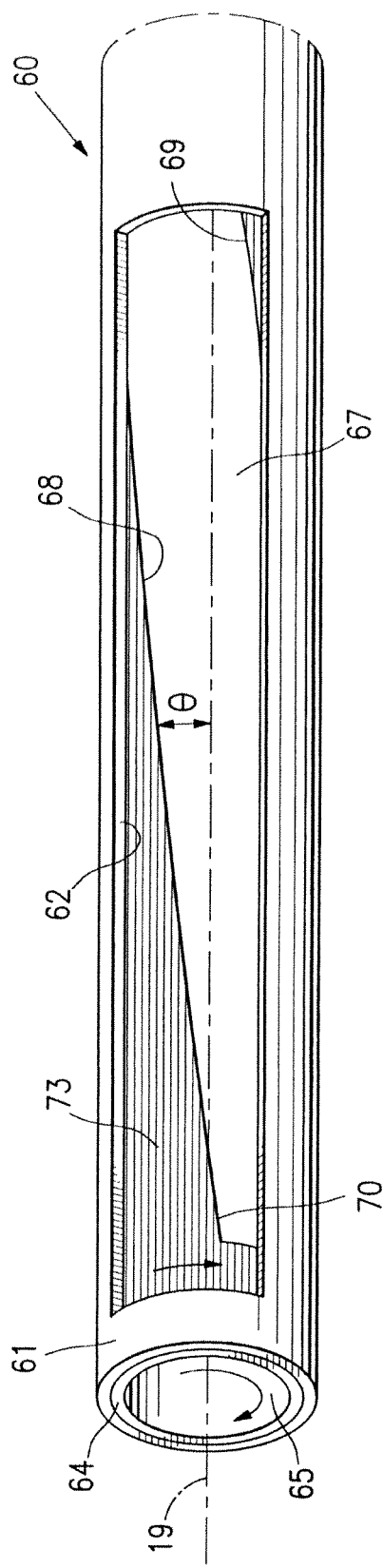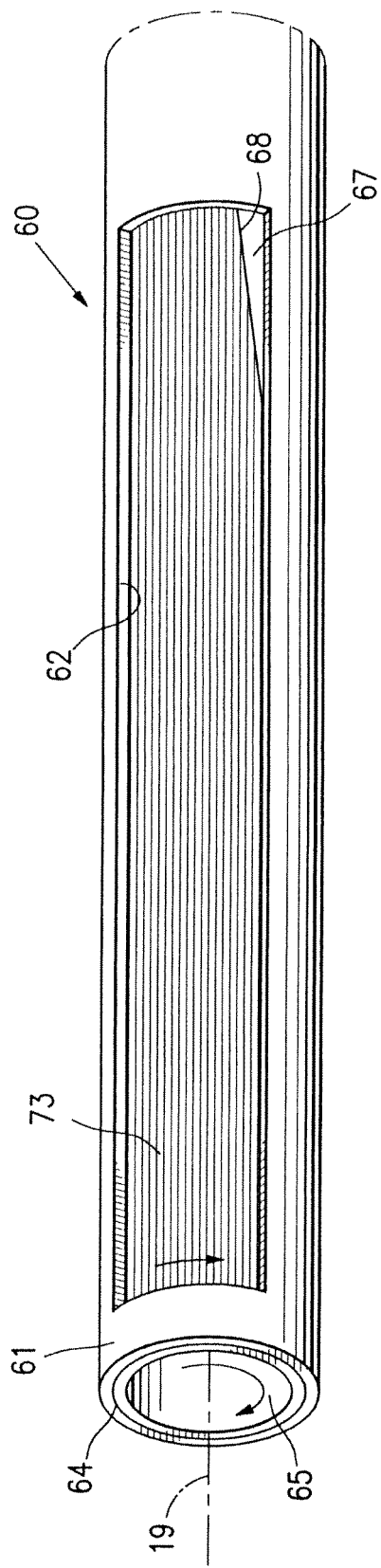

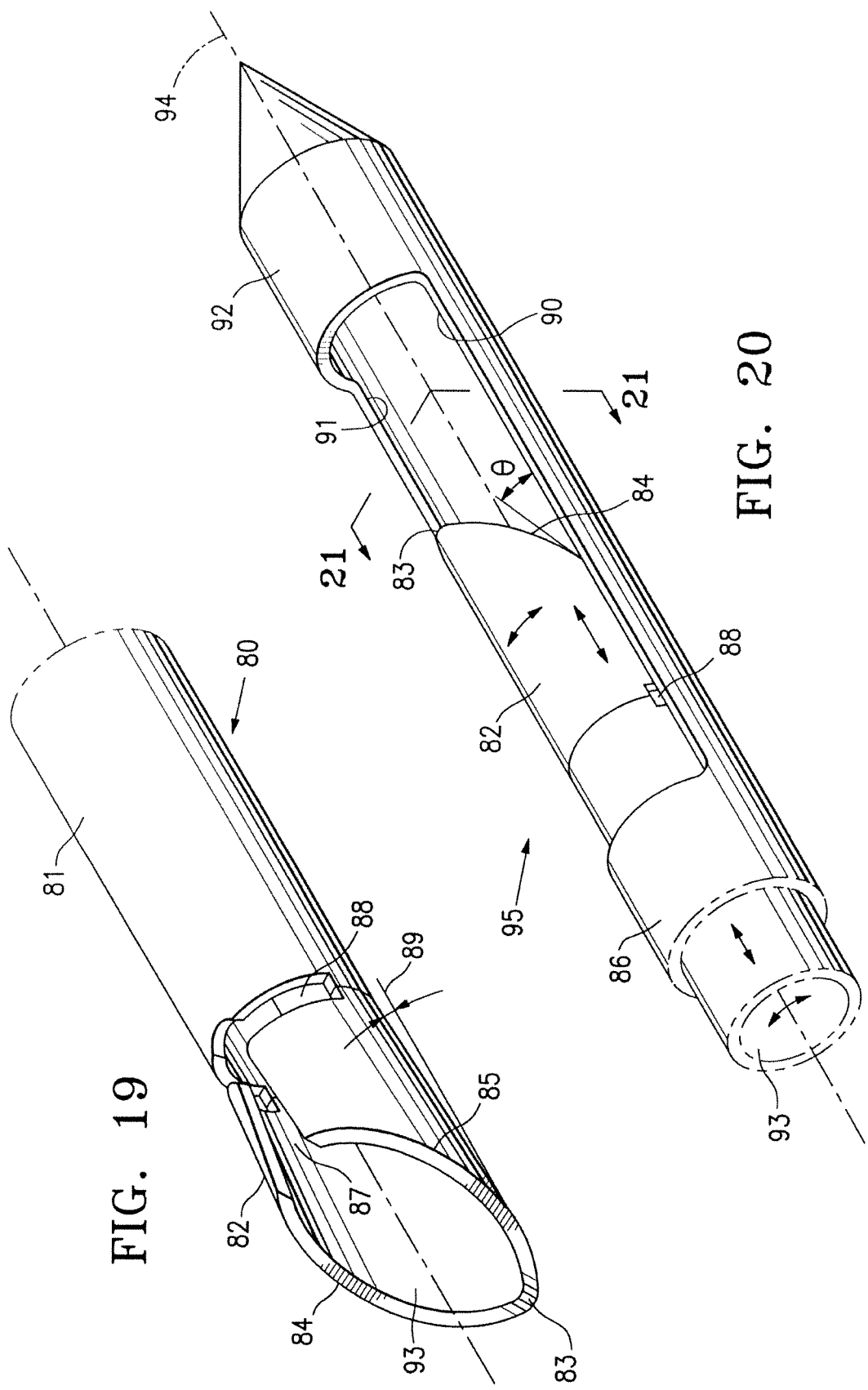

BIOPSY DEVICE WITH INNER CUTTING MEMBER

RELATED APPLICATIONS

This application is a continuation of application Ser. No. 10/642,406, filed Aug. 15, 2003 now U.S. Pat. No. 7,819,819, which is a continuation-in-part of application Ser. No. 10/374,915, filed Feb. 24, 2003, now U.S. Pat. No. 7,189,206, all of which are incorporated herein in their entirety.

FIELD OF THE INVENTION

The present invention relates generally to tissue removing devices such as biopsy devices and the methods of using such devices. More specifically, it is directed to a device and method for accessing and removing pathologically suspect tissue from within a patient's body.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to extract the biopsy specimen therefrom.

Electrosurgical techniques have been used in a variety of biopsy procedures. In electrosurgery, high frequency electrical energy is typically applied to patient tissue through an active electrode, the electrical circuit being completed by a return electrode in contact with the patent's tissue. Electrical energy flowing through the tissue from the active electrode is effective to ablate tissue near the active electrode, forming an opening in the tissue and so allowing insertion of the instrument into a patient's body. A return electrode may be placed on the exterior of the patient's body or may be incorporated into the device itself. The return electrode is typically attached to the patient at a point remote from where the primary or active electrode contacts the tissue. However, in the case of a bipolar electrode for example, the return electrode may be disposed near to the active electrode. An electrosurgical biopsy instrument is disclosed and claimed in U.S. patent application Ser. No. 09/159,467 for "Electrosurgical Biopsy Device and Method," now U.S. Pat. No. 6,261,241, assigned to the assignee of the present application, and which is hereby incorporated by reference in its entirety.

While these electrosurgical biopsy devices have been found to be effective in many instances, they are not suitable for use in conjunction with magnetic resonance imaging.

SUMMARY OF THE INVENTION

This invention is directed to biopsy devices and methods for accessing and collecting tissue from a patient utilizing such devices. These devices provide access to a targeted tissue site and provide for the separation and capture of a tissue specimen from supporting tissue at the targeted site.

A tissue collection device having features of the invention includes an elongated probe with an outer member having a tissue penetrating distal tip, a tubular portion proximal to the distal tip, an inner lumen extending within the tubular portion and an opened section or aperture in the tubular portion which provides access to tissue at the targeted site. The probe includes an elongated tissue-cutting member which is preferably at least in part cylindrically shaped and which is slidably disposed within the inner lumen of the outer tubular member. The tissue cutting member is provided with at least one tissue cutting surface which is configured to sever tissue extending into the probe through the open section or aperture of the outer member. The cutting edge on the tissue cutting member may be configured to rotationally and/or longitudinally move to cut a tissue specimen. The cutting movement may include oscillating rotational motion and/or reciprocating longitudinal motion to sever specimen tissue from supporting tissue at the targeted site. The cutting surfaces or edges are radially spaced from a longitudinal axis of the tissue collection device and are generally longitudinally oriented over a length thereof, preferably at an angle in the cutting direction (hereinafter the cutting angle) of less than 90° from the longitudinal axis or from a longitudinally oriented edge of the tissue receiving aperture of the outer tubular member. The cutting edge takes the general curvature of the cylindrical body forming the cutting member.

In one embodiment of the invention, the cutting member has an inner lumen preferably extending to the proximal end thereof for tissue specimen removal. Mechanical withdrawal of the tissue specimen may be employed or the proximal end of the cutting member may be configured to be in fluid communication with a vacuum source to aspirate the severed tissue specimen through the inner lumen of the cutting member to a tissue collection station. A higher fluid pressure may be maintained in the inner lumen of the cutting member distal to the tissue specimen to aid in transporting the specimen proximally through the inner lumen. In this manner, the mechanical withdrawal and/or the vacuum on the proximal end of the specimen and a higher pressure on the distal end of the specimen cn move the specimen through the inner lumen of the cutting member to a tissue collection station.

In at least one embodiment, the probe of the tissue collection device is secured, preferably releasably secured, to a drive housing provided with at least one drive unit. The tissue cutting member is operatively connected to the at least one drive unit to provide the desired cutting motion. The proximal end of the outer cannula is releasably secured to the drive housing so that the orientation of the outer cannula with respect to the housing can be selected before the probe is inserted into the patient.

The probe may be provided with a tubular tissue accessing cannula which is concentrically disposed between the outer tubular member and the tissue cutting member and a distal portion of the accessing cannula is provided with a tissue accessing aperture. The tissue accessing cannula is connected by its proximal end to a drive unit within the housing to rotate the cannula to adjust the orientation of the tissue receiving aperture about the longitudinal axis of the accessing cannula. A proximal extremity of the cutting member is connected to a second drive unit or units to effect the rotation and any longitudinal motion desired for cutting the tissue specimen A method of cutting and collecting a tissue specimen with a tissue collection device embodying features of the invention includes advancing such a device at least partially into tissue at a desired site within the patient's body with the tissue penetrating distal tip of the outer cannula disposed distal to the tissue to be separated from the target site. The inner lumen of the accessing cannula or the interior of the outer tubular member is exposed to tissue through the accessing aperture and the tissue is drawn into the accessing cannula by applying a vacuum to the inner lumen. A cutting member within the probe of the biopsy device may then be moved to cut a tissue specimen from supporting tissue at the target site by rotational and/or longitudinal motions which preferably includes oscillating rotational movement and/or reciprocating longitudinal movement. Vacuum may be applied to the inner lumen of the cutting member, to pull or aspirate the tissue sample proximally. In addition, or alternatively, a higher fluid pressure may be maintained in a distal portion of the inner lumen distal to the specimen to push the tissue specimen proximally or the specimen may be mechanically withdrawn. Fluid pressure may include pressure from a liquid delivered into the interior of the device, such as a physiological saline solution, and may include a gas, such as pressurized carbon dioxide, nitrogen or air, delivered into the interior of the device. Access to ambient air can also maintain a sufficiently high pressure differential to move the specimen through the inner lumen of the cutting member. Anesthetic may be injected to the target site through the outer cannula or the inner lumen of the cutting member. Upon removal from the patient, the tissue specimen may then be subjected to pathological examination. After acquisition of a tissue specimen or specimens, the biopsy device may be withdrawn from the patient.

The outer tubular member of the probe provides the support for the probe to enable precise location of the accessing port to the desired location at the target site with its longitudinal orientation being preset before the device is introduced into the patient. If an accessing cannula is provided with the biopsy device, the accessing cannula is rotated to further position the tissue accessing aperture to the desired specimen tissue and also to relocate the accessing aperture about or along the longitudinal axis of the device for taking further specimens. The cutting member quickly and cleanly severs the tissue specimen from the supporting tissue to provide a better tissue specimen for pathological examination.

These and other advantages of the invention will become more apparent from the following detailed description of the invention and the accompanying exemplary drawings.

BRIEF DESCRIPTION OF THE DRAWINGS

FIG. 2 is a perspective view of the distal portion of the outer member or cannula of the biopsy device shown in the FIG. 1.

FIG. 3 is a transverse view, partially in section, of the proximal end of the distal tip of the outer member shown in FIG. 2 taken along the lines 3-3.

FIG. 4 is a perspective view of the distal portion of the tissue accessing cannula of a biopsy device shown in FIG. 1.

FIG. 5 is a transverse cross-sectional view of the tissue accessing cannula shown FIG. 4 taken along the lines 5-5.

FIG. 6 is a perspective view of the distal portion of the tissue cutting member of the biopsy device shown in FIG. 1.

FIG. 7 is a transverse cross-sectional view of the tissue cutting member shown in FIG. 6 taken along the lines 7-7.

FIGS. 9A and 9B are schematic transverse cross-sectional views of the probe shown in FIG. 1 in open and closed configurations respectively with the aperture of the tissue accessing device opening to the left.

FIGS. 10A and 10B are schematic transverse cross-sectional views of the probe shown in FIG. 1 in open and closed configurations respectively with the aperture of the tissue accessing device opening upwardly.

FIGS. 11A and 11B are schematic transverse cross-sectional views of the probe shown in FIG. 1 in open and closed configurations respectively with the aperture of the tissue accessing device opening to the right.

FIGS. 12A and 12B are schematic transverse cross-sectional views of the probe shown in FIG. 1 in open and closed configurations respectively with the aperture of the tissue accessing device opening downwardly.

FIG. 13 is a perspective view of the distal portion of an alternative design for the probe embodying features of the invention in a closed condition.

FIG. 14 is a top plan view of the tissue cutting member of the probe shown in FIG. 13 with an inclined cutting edge.

FIG. 15 is a perspective view of the probe shown in FIG. 13 partially open.

FIG. 16 is a perspective view of the probe shown in FIG. 13 with the leading distal cutting edge depicted.

FIG. 17 is a perspective view of the probe shown in FIG. 13 further rotated from that shown in FIG. 16.

FIG. 18 is a perspective view of the probe shown in FIG. 13 with the aperture of the outer member almost closed.

FIG. 19 is a perspective view of the distal portion of a tissue cutting member of a biopsy device embodying features of the invention.

FIG. 20 is a perspective view of the cutting member of the biopsy device shown in FIG. 19 slidably disposed within an outer cannula of the biopsy device.

DETAILED DESCRIPTION OF THE INVENTION

Figure 1:
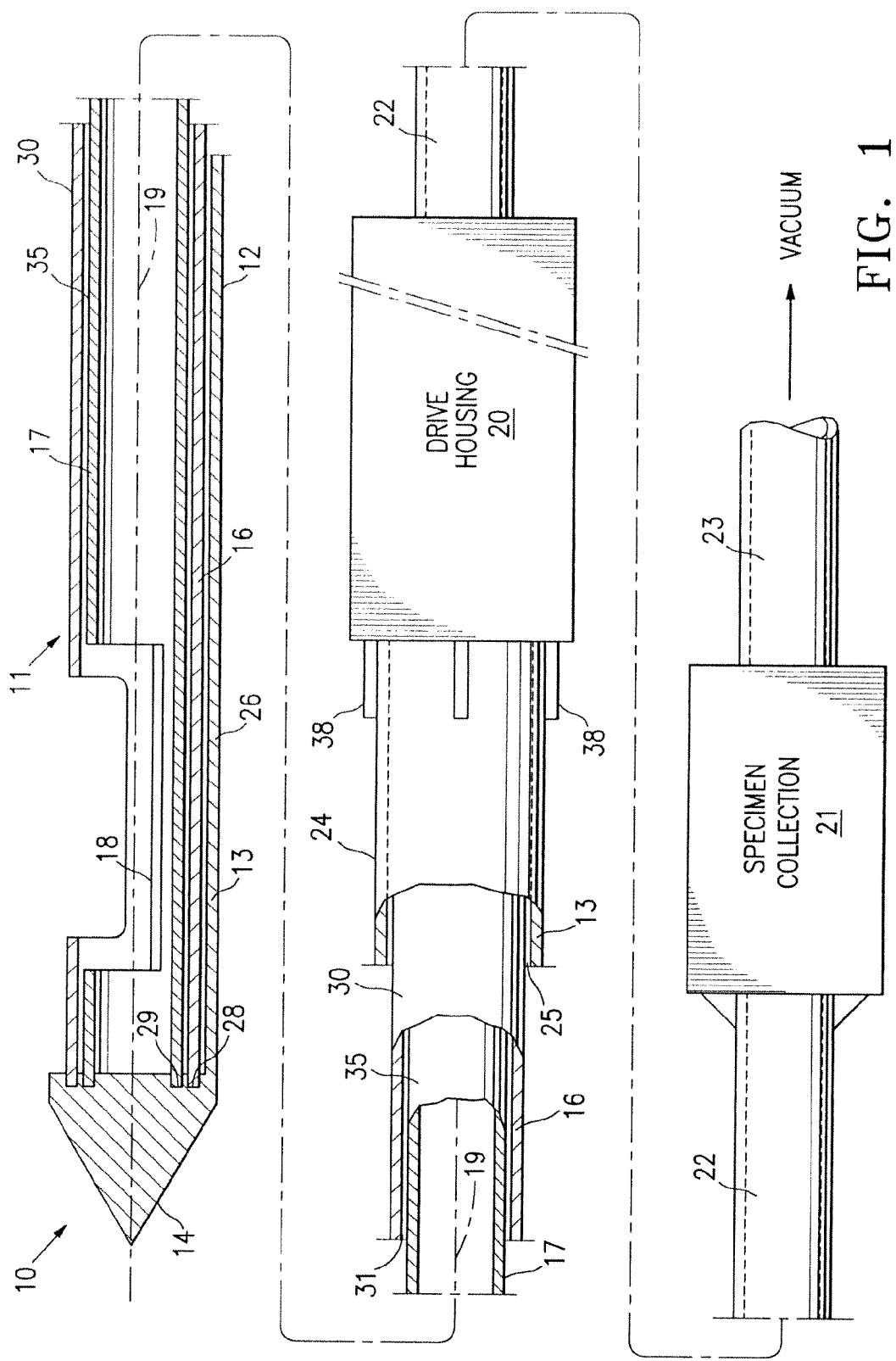
FIG. 1 is an elevational view, partially in section, of an elongated tissue biopsy system having features of the invention.

FIGS. 1-7 illustrate a system 10 which includes a biopsy device 11 embodying features of the invention. The biopsy device 11 generally includes an elongated shaft or probe 12 having an outer tubular member or cannula 13 with a tissue penetrating tip 14 on the distal end thereof and an open tissue accessing region 15, a tissue accessing cannula 16 and a tissue-cutting member 17 with a tissue cutting edge 18 which is preferably at an angle θ with respect to the longitudinal axis 19. The proximal end of the outer tubular member 13 is releasably secured to a drive housing 20 to provide a plurality of discrete orientations to the outer member 13. The housing 20 is provided with a drive unit (not shown) configured to provide motion to the tissue accessing cannula 16 and the tissue cutting member 17. A tissue specimen collection station 21 is connected in a fluid flow relationship with the tissue cutting member 17 through conduit 22 and is connected to a vacuum source (not shown) through conduit 23.

As shown in more detail in FIG. 2 the outer member 13 has an elongated tubular body 24 with an inner lumen 25 which is configured to receive and support the accessing cannula 15. The distal end of inner lumen 25 opens to the tissue accessing space between the distal end of the tubular body 24 and the proximal end of tissue penetrating tip 14. A connecting strut or wall portion 26 extends between the tissue penetrating distal tip 14 and the tubular body 24 of the outer member 13. As shown in FIG. 3, the proximal end 27 of the penetrating tip 14 is provided with a first circular groove 28 which is configured to receive the distal end of the accessing cannula 16 as shown in FIGS. 1 and 3 and a second circular groove 29 which is configured to receive the distal end of tissue cutting member 17. The penetrating distal tip 14 may have a variety of tip shapes in addition to the conical shape shown and may have an arcuate RF electrode such as disclosed in U.S. Pat. No. 6,261,241, and U.S. Pat. No. 6,471,700, both assigned to the present assignee and both are incorporated herein in their entirety. The width and length of the strut 26 is sufficient to provide required support to the distal tip 14 and may vary depending upon the strength of the material from which it is made. A stiffening rib may be provided to the underside of the strut for structural stiffness. Multiple struts may be used, provided that a large enough opening is available for tissue access to the aperture 27 of the accessing cannula 15.

As best shown in FIGS. 4 and 5, the accessing cannula 15 has a tubular body 30 which defines at least in part the tissue receiving aperture 27. The tubular body 30 has an inner lumen 31 which is configured to slidably receive the tissue cutting member 17. The aperture 27 is configured to receive tissue for the specimen of suitable size. The arcuate length of the side edges 32 and 33 forming the aperture 27. The accessing cannula 16 is configured at its proximal end to be operatively connected to a drive unit (not shown) to rotate the tubular body 30 about longitudinal axis 34 to provide a desired orientation to the aperture 27.

The tissue cutting member 17, as depicted in FIGS. 6 and 7, is formed of tubular member 35 which has an inner lumen 36 and which has an arcuate wall portion 37 forming side cutting edge 18. The tissue cutting edge 18 may be a sharpened edge of the arcuate wall portion 37 or it may be a blade (not shown) secured to the edge. The cutting edge 18 should be longer than the length of the aperture to ensure complete severance of the tissue specimen from the supporting tissue at the target site upon rotation of the cutting edge 18. The tissue cutting member 17 is rotated to effect tissue cutting by cutting edge 18, but the member may also be provided with reciprocating longitudinal movement in addition to the rotational movement thereof to provide a cleaner tissue cut. Both edges of the arcuate wall portion 37 may be sharpened or provided with blades for tissue cutting purposes. The cutting edge 18 is spaced radially from the longitudinal axis of the probe and inclined at an acute cutting angle $\theta$ with respect to the longitudinal axis 34.

Figure 8:
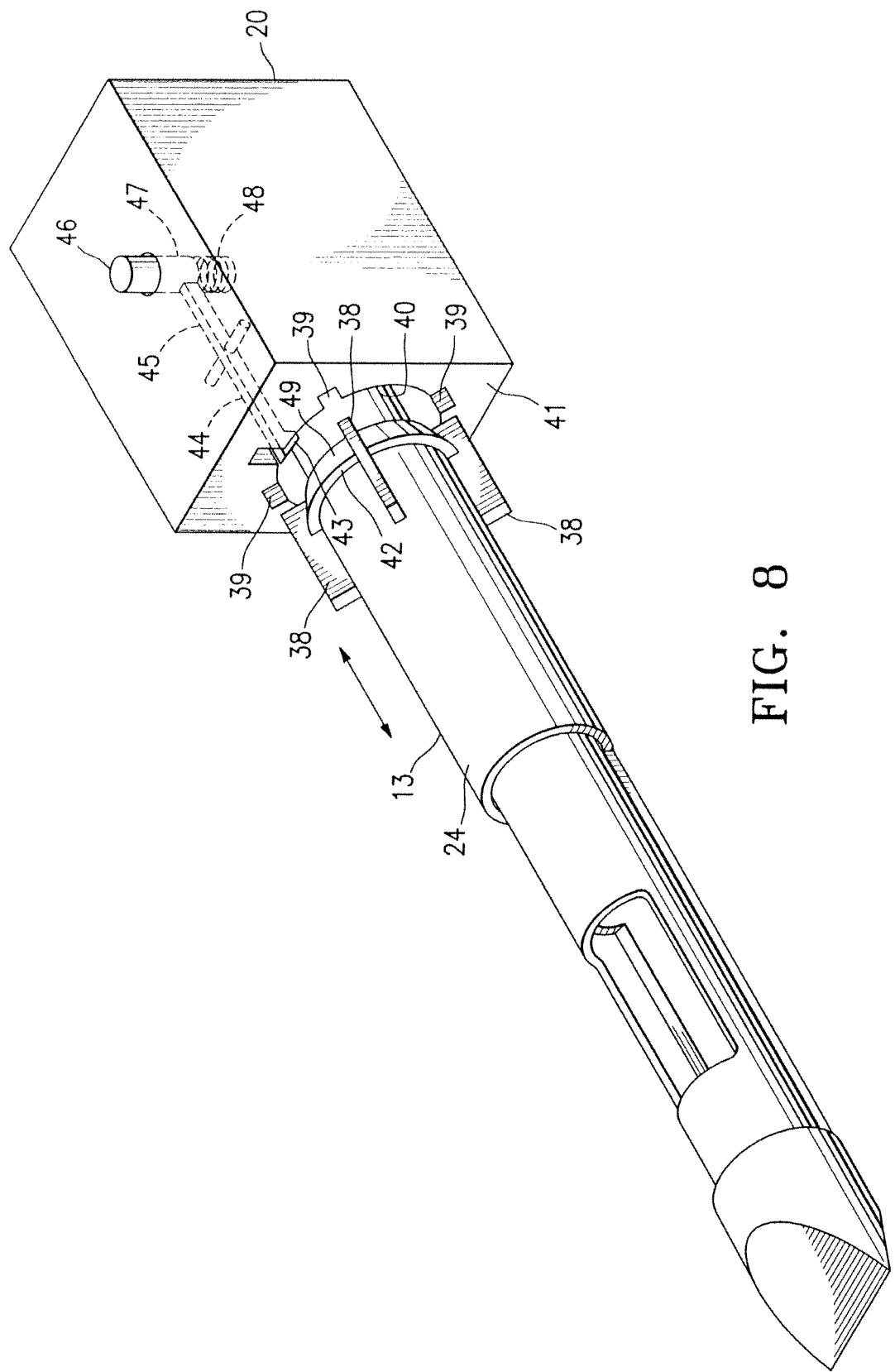
FIG. 8 is a perspective view of the proximal end of the biopsy device illustrating the releasable connection between the proximal end of the probe and the housing.

FIGS. 1 and 8 illustrate the releasable connection between the outer member 13 and the housing 20 to allow for a plurality of discrete orientations of the tissue receiving space of the outer member. As shown, the proximal end of the tubular portion 24 of outer member 13 is provided with a plurality of longitudinally extending upstanding ribs 38 spaced about the periphery of the tubular portion 24. A corresponding number of recessed passageways 39 are disposed about the opening 40 in the distal face 41 of housing 20 designed to receive the ribs 38. Arcuate ridges 42 are provided between the ribs 38 to receive tooth 43 of releasable locking mechanism 44 provided in the interior of housing 20. The mechanism 44 for releasably locking the proximal end of the outer member 13 may take a variety of configurations. The particular mechanism 44 shown in FIG. 8 is preferably manually operated by the fingers of the operating physician. The operator 45 is pivotally connected within the housing 20 at an intermediate location so that downward pressure on button 46 in the top portion of the housing 20 connected to elongated member 47 presses the proximal end of operator 45 raising the distal end and the tooth 43 to release the tooth 43 from the ridge 42 to allow for movement of the proximal end of tubular portion 24 of outer member 13 with respect to the housing 20. The distal end of the mechanism 44 is biased upwardly by spring 48 so that when the proximal end of the outer member 13 is inserted into opening 40 the tooth 43 rides up ramping surface 49 on the proximal end of the ridge 42 and seats and is locked on the front face of ridge 42.

The drive housing 20 and attached probe 11 allows the entire unit to be disposable. The drive units within the housing control the motion of the accessing cannula 16 to orient the aperture 27 and the motion of the cutting member 17 which may be rotation or rotation and longitudinal reciprocation. Other means (not shown) may provide mechanical and electrical power, vacuum, and control to the probe device. Examples of replaceable snap-in type drive units are disclosed in Burbank et al., U.S. patent application Ser. No. 10/179,933, "Apparatus and methods for Accessing a Body Site" hereby incorporated by reference in its entirety. Drive units such as that described in WO 02/069808 (which corresponds to co-pending U.S. application Ser. No. 09/707,022, filed Nov. 6, 2000 and U.S. application Ser. No. 09/864,021, filed May 23, 2001), which are incorporated herein by reference, may be readily modified by those skilled in the art to accommodate the movement of the accessing cannula 16 and the cutting member 17.

FIGS. 9A and 9B, 10A and 10B and 11A and 11B schematically illustrate the operation of the device 11 and the rotation of the probe 12 to discrete orientations. This series of sketches depict the sequencing of taking tissue specimens from below or the bottom side of a target site. In FIG. 9A the aperture 16 is open to the left with the arcuate wall portion 40 in a non cutting position. A vacuum is applied to the inner lumen 31 of the tissue cutting member 17 and tissue 50 (shown in phantom) from the target site is pulled into the interior of the accessing cannula 15 through the aperture 16. In FIG. 9B the arcuate portion 37 of tissue cutting member 17 is rotated to sever the aspirated tissue 50 from the supporting tissue at the target site with the cutting surface 18. The vacuum within the inner lumen 31 of the tissue cutting member 17 causes the tissue specimen to be drawn through the inner lumen and into the collection station 21 shown in FIG. 1. Positive pressure or even ambient conditions distal to the tissue specimen can facilitate tissue passing through the inner lumen 31. The accessing cannula 15 is then rotated so that the aperture 27 is facing upwardly as shown in FIG. 10A and as shown in FIG. 10B the procedure for cutting the tissue specimen is repeated. In FIGS. 11A and 11B the aperture 27 is open to the right and the procedure is again repeated for additional specimens. Other intermediate positions for the aperture 27 are possible. When the target site is accessed from the upper portion thereof, the probe device 11 is released from the housing 20 and then is inverted or turned through 180° so that the strut 26 is on top as shown in FIGS. 12A and 12B with the aperture 27 open downwardly. The housing 20, not shown in these drawings, may remain in the same orientation. The same motion for the accessing cannula 16 as described above may be used to obtain a similar series of tissue specimens from the top of the target site. If the target site is large enough, the probe may pass through the site and accessing may occur from within the interior of the target site in the same or similar manner as that discussed above for accessing the tissue from the top or bottom of the tissue site.

FIGS. 13-18 illustrate a probe 60 for a biopsy device embodying features of the invention. In probe 60 the outer member or cannula 61 has a tissue receiving aperture 62 for receiving tissue from the target site. The outer member 61 has a sharp distal tip 63 shown in phantom which is configured to easily penetrate through tissue to the target site. Tissue cutting member 64 is rotatably disposed within outer member 61 and has a proximal end (not shown) operatively connected to one or more drive units within housing (not shown) for imparting cutting motion thereto such as previously described herein. The inner lumen 65 of tissue cutting member 64 is configured for fluid communication with a vacuum source (not shown) to urge a tissue specimen through the inner lumen 65. As mentioned with the description of the embodiment shown in FIG. 1-7, positive pressure or even ambient conditions will aid in passing the severed tissue through the inner lumen 65 of tissue cutting member 64. The tissue cutting member 64 has an aperture 67 as shown in FIG. 14 defined in part by cutting edge 68 and non-cutting edge 69. The cutting surface is longitudinally oriented at an angle with respect to the longitudinal axis of the tissue cutting member 64. The cutting surface or edge 68 has a distal leading cutting edge portion 70 and a proximal trailing cutting edge portion 71. This tissue cutting member structure provides better application of vacuum to tissue at the target site and as a result provides better control of the tissue cutting. The cutting action for this embodiment is shown in the sequence shown in FIGS. 13 and 15-18. In FIG. 13, the aperture 62 of the outer member 61 is closed by the arcuate wall portion 73 of tissue cutting member 64. The non-cutting edge 69 of tissue cutting member 64 first appears at the distal end of aperture 67 as shown in FIG. 15. Application of vacuum begins to pull tissue from the target site into the interior of the tissue cutting member at the distal location. As the tissue cutting member 64 rotates (as shown in FIGS. 16-18) the non-cutting edge 69 first appears to allow tissue to be pulled into the inner lumen 65 of the tissue cutting member and the cutting edge 68 of the tissue cutting member follows, cutting off tissue pulled into the interior of the cutting member from the supporting tissue at the target site starting from the leading cutting edge portion 70 to the trailing proximal cutting edge portion 71 along the length of the aperture 67.

FIG. 19 illustrates a tissue cutting member 80 which embodies features of the invention and which has an elongated cylindrically shaped body 81 with a distal cutting section 82. The distal cutting section 82 has a beveled, needle-like distal tip 83 with a sharpened opposed edges 84 and 85 which facilitate cutting of the tissue specimen when the cutting member 80 is moved within the outer tubular member or cannula 86 (as shown in FIG. 20). A longitudinal slot 87, which preferably tapers to smaller transverse dimension in the proximal direction, is provided in the distal cutting section 82 at the proximal ends of the sharpened edges 84 and 85 and a transverse slot 88 is provided at the proximal end of slot 87 to facilitate slight flaring of the distal cutting section 82 as shown by line 89. The outward bias of the sharpened edges 84 and 85 ensures that these edges engage the longitudinal edges 90 and 91 of the accessing aperture 92 of the outer cannula 86 as shown in FIG. 20 to provide a scissor-like cutting motion for severing a tissue specimen from supporting tissue at the target biopsy site.

Figure 21A:
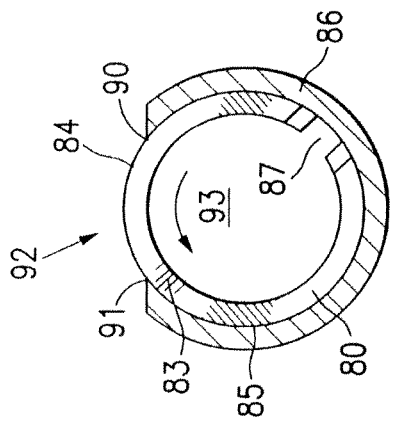
FIGS. 21A, 21B and 21C are schematic transverse cross-sectional views taken along the lines 21-21 shown in FIG. 20 depicting the reciprocating motion of the cutting member.
Figure 21B:
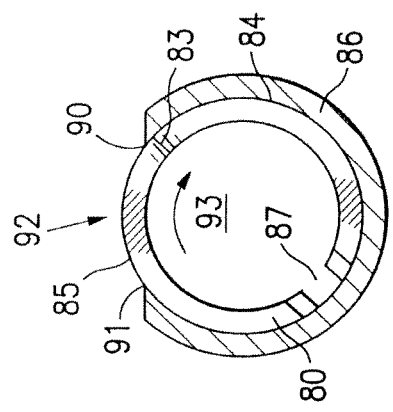
Figure 21C:
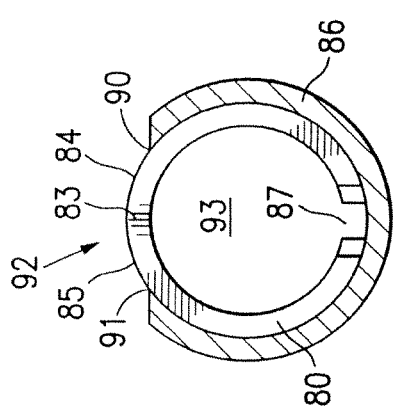
Figure 22:
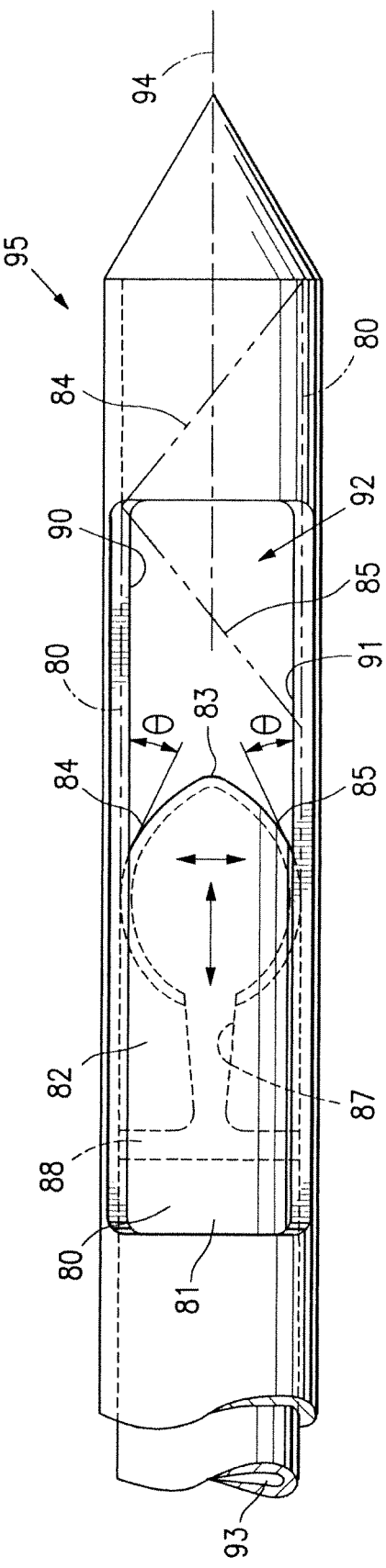
FIG. 22 is a plan view of the tissue receiving aperture in the distal portion of the device illustrated in FIG. 20 to further illustrate the reciprocating rotational and longitudinal motion of the cutting member shown in FIG. 20.

FIGS. 21A-21C and FIG. 22 illustrate the oscillating and longitudinal motions of the cutting member 80 within the outer cannula 86 as the cutting member is advanced distally. FIGS. 21A-21C are highly schematic transverse cross-sectional views illustrating the rotational oscillation. In FIG. 21A the beveled tip 83 is centrally positioned within the accessing aperture 92. In FIG. 22B the cutting member 80 has rotated toward the cutting edge 90 of aperture 92 with cutting edge 84 of the cutting member 80 engaging the edge 90 in a scissor-like fashion. In FIG. 21C the cutting member has rotated to the cutting edge 91 of aperture 92 with the cutting edge 85 of the cutting member 80 engaging the cutting edge 91 in a scissor-like fashion. As shown more clearly in FIG. 22, the cutting member 80 moves longitudinally as it is rotationally oscillated so that the flared cutting edges 84 and 85 engage the edges 90 and 91 of the length of the accessing aperture 92 to provide scissor-like, tissue cutting action. The cutting action preferably continues until the beveled tip 83 has completely traversed the aperture 92 and the tissue specimen has been completely severed from supporting tissue at the biopsy site. A vacuum may be applied to the inner lumen 93 of the cutting member 80 to aspirate the severed tissue specimen to the proximal end of the biopsy device where the specimen may be removed. Positive pressure or access to ambient conditions may be provided in the distal tip of the outer cannula 86 to aid in the specimen transfer through the inner lumen 93 of the cutting member 80. The cutting edges 84 and 85 have cutting angles $\theta$ with respect to cutting edges 90 and 91 (which are generally parallel to the longitudinal axis 94) of about 20° to about 80°, preferably about 30° to about 75°, over most of the length of the cutting edges 84 and 85. However, at the proximal and distal ends of the beveled tip, the cutting angle may approach 90°.

The cutting member 80 is positioned in its most forward position closing off aperture 82 when the biopsy device 93 is advanced to the desired biopsy site. The cutting member is then pulled proximally to expose a desired length of the aperture 82 which controls the length of the specimen to be severed from the supporting tissue. The cutting member 80 is then advanced distally with a side-to-side oscillation to sever tissue drawn or otherwise extending into the interior of the outer cannula 86. The cutting member 80 may also be provided with longitudinal reciprocating motion to aid in severing the tissue specimen from the supporting tissue at the biopsy site.

The elongated shaft or probe of the biopsy device has a length of about 3 to about 15 cm, preferably, about 5 to about 13 cm, and more specifically, about 8 to about 9 cm for breast biopsy use. To assist in properly locating the probe of the device during advancement thereof into a patient's body, (as described below), the distal extremity of the various members may be provided with markers at desirable locations that provide enhanced visualization by eye, by ultrasound, by X-ray, MRI or other imaging or visualization means. Manual palpation may also be employed. An echogenic polymer coating that increases contrast resolution in ultrasound imaging devices (such as ECHOCOAT™ by STS Biopolymers, of Henrietta, N.Y.) is suitable for ultrasonic visualization. Radiopaque markers may be made with, for example, stainless steel, platinum, gold, iridium, tantalum, tungsten, silver, rhodium, nickel, bismuth, other radiopaque metals, alloys and oxides of these metals. In addition, the surfaces of the device in contact with tissue or other components of the device may be provided with a suitable lubricious coating such as a hydrophilic material or a fluoropolymer.

The outer member or cannula, the accessing cannula and the tissue cutting member are preferably formed of stainless steel. However, other high strength materials such as MP35N, other cobalt-chromium alloys, NiTi alloys, ceramics, glasses, and high strength polymeric materials or combinations thereof may be suitable.

A patient's skin usually must be breached in order to gain access to a body site where a tissue specimen is to be obtained. A scalpel or other surgical instrument may be used to make an initial incision in the skin. After the specimens have been taken, the biopsy device may be removed from the patient. The entire device may be removed; however, in some embodiments, the outer member may remain within a patient's body to aid, for example, in the acquisition of further tissue specimens and in the placement of markers at the site from which a tissue sample was taken. In addition, it will be readily appreciated that other types of instruments may be inserted into the tissue site through the fixed outer cannula or accessing cannula in addition to or in place of the instruments described above.

While particular forms of the invention have been illustrated and described herein, it will be apparent that various modifications and improvements can be made to the invention. For example, while the various embodiments of the invention have been described herein in terms of a biopsy device, it should be apparent that the devices and methods of utilizing the device may be employed to remove tissue for purposes other than for biopsy, i.e. for treatment or other diagnoses. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety.

What is claimed is:

1. A tissue biopsy device for accessing and severing a tissue specimen from supporting tissue at a target site within a patient, comprising:
   a. an elongated probe member which has a longitudinal axis, which has an inner lumen extending therein, which has a tissue penetrating distal tip and which has a tissue receiving aperture proximal to the tissue penetrating distal tip, the tissue receiving aperture being defined by a proximal closed end, a distal closed end, and longitudinal sides that extend between the proximal closed end and the distal closed end, the longitudinal sides being configured to define at least one longitudinally oriented tissue cutting edge; and
   b. an elongated tissue cutting member which is disposed within the inner lumen of the elongated probe member and configured for cutting movements therein, which has a distal portion with a tissue cutting edge radially spaced from and is at least in part oriented at an acute cutting angle with respect to the at least one longitudinally oriented tissue cutting edge defining in part the aperture of the probe member and which is configured to be connected to at least one drive unit to oscillate and distally advance the tissue cutting member relative to the at least one longitudinally oriented tissue cutting edge to sever from supporting tissue a tissue specimen tissue extending into the tissue receiving aperture of the elongated probe member,
   wherein the elongated tissue cutting member has a beveled distal tip having a pair of cutting edges, one cutting edge configured to engage a first cutting edge of the elongated probe member and a second cutting edge configured to engage a second cutting edge of the elongated probe member, and
   wherein the beveled distal tip of the tissue cutting member has a longitudinally oriented slot which separates the tissue cutting edges of the tissue cutting member.

2. The biopsy device of claim 1 wherein the longitudinally oriented slot tapers in the proximal direction to smaller transverse dimensions.

3. The biopsy device of claim 1 wherein the distal portion of the tissue cutting member has a transversely oriented slot proximal to the beveled tip.

\* \* \* \* \*